(12) United States Patent
Lease (10) Patent No.: US 8,574,589 B2
(45) Date of Patent: Nov. 5, 2013

(54) ANTIGEN PURIFICATION PROCESS FOR PERTACTIN ANTIGEN

(75) Inventor: Christian A. Lease, Concord, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/320,003

(22) PCT Filed: May 10, 2010

(86) PCT No.: PCT/IB2010/001169
§ 371 (c)(1),
(2), (4) Date: Feb. 22, 2012

(87) PCT Pub. No.: WO2010/131111
PCT Pub. Date: Nov. 18, 2010

(65) Prior Publication Data
US 2012/0269847 A1    Oct. 25, 2012

Related U.S. Application Data (60) Provisional application No. 61/215,980, filed on May 11, 2009.

(51) Int. Cl.
*A61K 39/00* (2006.01)

(52) U.S. Cl.
USPC ............... 424/203.1; 424/201.1; 424/254.1; 530/413

(58) Field of Classification Search
None
See application file for complete search history.

(56) References Cited

U.S. PATENT DOCUMENTS

| | | | | |
|---|---|---|---|---|
| 5,276,142 | A * | 1/1994 | Gotto | 530/413 |
| 5,667,787 | A * | 9/1997 | Jackson et al. | 424/253.1 |
| 6,106,842 | A * | 8/2000 | Capiau et al. | 424/240.1 |
| 6,197,548 | B1 * | 3/2001 | Clare et al. | 435/69.3 |
| 7,070,779 | B2 * | 7/2006 | Boursaux-Eude et al. | 424/184.1 |
| 7,308,864 | B1 * | 12/2007 | Catner | 116/173 |
| 8,007,807 | B2 * | 8/2011 | Borkowski | 424/184.1 |
| 8,299,210 | B2 * | 10/2012 | Jungbluth et al. | 530/324 |
| 2002/0119161 | A1 * | 8/2002 | Suehara et al. | 424/185.1 |
| 2003/0133941 | A1 * | 7/2003 | Suehara et al. | 424/185.1 |
| 2004/0208898 | A1 * | 10/2004 | Florent et al. | 424/202.1 |
| 2005/0100553 | A1 * | 5/2005 | Blake et al. | 424/190.1 |
| 2006/0204955 | A1 * | 9/2006 | Blake et al. | 435/5 |
| 2007/0116711 | A1 * | 5/2007 | Castado et al. | 424/190.1 |
| 2009/0215113 | A1 * | 8/2009 | Jungbluth et al. | 435/68.1 |
| 2010/0040647 | A1 * | 2/2010 | De Hemptinne et al. | 424/197.11 |

FOREIGN PATENT DOCUMENTS

| | | |
|---|---|---|
| WO | WO-91/15505 | 10/1991 |
| WO | WO-02/083710 | 10/2002 |
| WO | WO-2005/032584 | 4/2005 |
| WO | WO-2007/139470 | 12/2007 |
| WO | 2009016651 | * 2/2009 |

OTHER PUBLICATIONS

Morbidity and Mortality Weekly Report, Mar. 28, 1997, pp. 1-25 with cover sheet, table of contents and final sheet, Pertussis Vacination: Use of Acellular Pertussis Vaccines Among Infants and Young Children. (total of 32 pages).*

(Continued)

*Primary Examiner* — Albert Navarro
*Assistant Examiner* — Ginny Portner
(74) *Attorney, Agent, or Firm* — Helen Lee; Otis Littlefield (57) ABSTRACT

*Bordetella pertussis* p69 antigen is purified by immobilized metal affinity chromatography.

12 Claims, 2 Drawing Sheets

(56) References Cited

OTHER PUBLICATIONS

Hijnen et al, 2005, Protein Expression and Purification, vol. 41(2005), pp. 106-112, The Bordetella pertussis virulence factor P.69 treatins its immunological properties after overproduction in *Escherichia coli*.*

Hijnen, Marcel et al, Chapter3, 2006, 13 pages , cover sheet plus numbered pp. 50-61.*

Sheu eta l. (2001). "Characteristics and potency of an acellular pertussis vaccine composed of pertussis toxin, filamentous hemagglutinin, and Pertactin. J.," Microbiol. Immunol. Infect. 34: 243-251.

Westra et al. (2001). "Immobilised metal-ion affinity chromatography purification of histidine-tagged recombinant proteins: a wash step with a low concentration of EDTA," J Chromatogr B Biomed Sci Appl. 760(1):129-36.

Zhao et al. (2009). "Immunogenicity of recombinant protective antigen and efficacy against intranasal challenge with Bordetella bronchiseptica," Vaccine. 27(18):2523-8. Epub Oct. 11, 2008.

International Search Report mailed Sep. 30, 2010, for PCT/IB2010/001169 filed May 10, 2010, 6 pages.

International Preliminary Report on Patentability dated Aug. 26, 2011, for PCT/IB2010/001169 filed May 10, 2010, 8 pages.

* cited by examiner

ANTIGEN PURIFICATION PROCESS FOR PERTACTIN ANTIGEN

CROSS REFERENCE TO RELATED APPLICATIONS

This application is a U.S. National Phase patent application of PCT/IB2010/001169, filed May 10, 2010, which claims priority to U.S. Provisional patent application Ser. No. 61/215,980 filed May 11, 2009, all of which are hereby incorporated by reference in the present disclosure in their entirety.

This application claims the benefit of U.S. provisional application 61/215,980 filed 11 May 2009, the complete contents of which are incorporated herein by reference.

TECHNICAL FIELD

This invention relates to processes for purifying 69 kDa pertactin protein from *Bordetella* bacteria.

BACKGROUND ART

*Bordetella pertussis* is the causative agent of whooping cough. Vaccines against whooping cough have been available for many years and have been successful in reducing the disease. The vaccines are either whole-cell (wP), based inactivated *B. pertussis* cells, or acellular (aP), based on purified *B. pertussis* antigens. The present invention relates to methods for purifying antigens suitable for use in acellular vaccines.

Current aP vaccines include the INFANRIX™ series, PEDIARIX™ and the BOOSTRIX™ series (all from GSK) and TRIPEDIA™, DAPTACEL™ and ADACEL™ (all from Sanofi Pasteur). These include one or more of the following *B. pertussis* antigens: pertussis toxin (PT), filamentous hemagglutinin (FHA), the 69 kDa pertactin protein (p69), and fimbrial agglutinogens (FIM). Using at least the three PT, FHA and p69 antigens is usual.

References 1 & 2 disclose a process for preparing PT and FHA. After cell growth the culture medium contains PT and FHA. These two antigens are adsorbed onto a solid support (e.g. Perlite) and are then selectively eluted. The two antigens are then each further purified by adsorption onto a hydroxyapatite column. The antigens are then inactivated using glutaraldehyde or formaldehyde.

Reference 3 discloses a process for preparing p69. The p69 antigen is precipitated using ammonium sulfate, either before or after perlite adsorption of PT and FHA. It is then further purified using hydroxyapatite and/or Q-Sepharose.

Reference 4 uses a combination of the methods of references 1 and 3 to purify the p69, PT and FHA antigens to give an aP vaccine. A similar procedure is disclosed in reference 5.

The PT and FHA antigens in the INFANRIX™ products are extracted from fermentation broth by adsorption on hydroxyapatite gel and are then further purified by hydrophobic, affinity and size exclusion chromatography. The p69 antigen in the INFANRIX™ products is extracted from the cells by heat treatment and flocculation using barium chloride and is then further purified by ion exchange, hydrophobic and size exclusion chromatography.

Various methods for purifying FHA, p69, PT and FIM antigens are disclosed in reference 6. Calcium ions are added to a *B. pertussis* culture containing excess phosphate ions, and the methods are based on the differential adsorption of the various antigens to the calcium phosphate that is formed in situ.

It is an object of the invention to provide further and improved methods for purifying p69 from *Bordetella pertussis*, to provide an antigen for manufacturing acellular whooping cough vaccines.

DISCLOSURE OF THE INVENTION

It has been found that p69 binds reversibly to immobilised metal ions and can thus be purified using the IMAC technique (immobilised metal affinity chromatography). The use of IMAC, when compared to the known purification processes, provides increased recovery yields, shorter processing time, greater consistency, easier implementation and high purity.

The invention provides a process for purifying *B. pertussis* p69 antigen from a mixture, comprising steps of: (a) contacting the mixture with a support comprising an immobilised metal ion, to give an eluate and a p69-containing retentate; (b) eluting p69 from the retentate to provide purified p69.

The invention also provides a process for purifying p69 antigen from *Bordetella pertussis* bacteria, comprising steps of: (a) separating a culture of *Bordetella pertussis* cells into a supernatant liquid and pertactin-containing cellular solids; (b) treating the cellular solids to release p69 pertactin therein; (c) contacting the released p69 with a support comprising an immobilised metal ion, to give an eluate and a p69-containing retentate; and (d) eluting p69 from the retentate to provide purified p69.

The Source of p69

A culture of *B. pertussis* cells can be separated into aqueous material and cellular solids. The cellular solids are the source of the final purified p69 antigen. Separation can be achieved by various methods. For instance, solids in the culture can be allowed to settle under gravity and the aqueous material can then be removed by decanting or by aspiration. Typically, however, centrifugation is used, to give a solid pellet and a centrate which can easily be separated. The pellet includes *B. pertussis* cells and other insoluble materials and contains pertactin. The centrate includes culture medium and any components released by the bacteria during culture. A useful centrifugation procedure uses disk stack continuous centrifugation. Suitable flow rates for this procedure may be in the range of 200-1000 kg/hr e.g. 300-800 kg/hr, 400-600 kg/hr, or about 500 kg/hr.

The cellular solids can be treated to release p69 pertactin to facilitate its purification. This release can be achieved by various techniques. For example, it can be released from the cell surface by acid treatment [7] or heat treatment [8]. Heat treatment is a convenient way to effect release e.g. by heating to about 60° C. for about 1 hour. Released p69 is soluble and so can readily be separated from remaining cellular solids. As noted above, separation can be achieved by various methods e.g. by the use of decanting, aspiration or centrifugation. Again, a useful procedure uses disk stack continuous centrifugation. Suitable flow rates for this procedure may be in the range of 50-600 kg/hr e.g. 100-500 kg/hr, 200-400 kg/hr, or about 300 kg/hr. The solid material (pellet) can be discarded, leaving a p69-containing supernatant.

The supernatant liquid contains p69 pertactin and can be subjected to IMAC according to the invention. Prior to IMAC, however, the liquid may be further treated e.g. by one or more steps of filtration and/or concentration, etc.

After release of p69, but before IMAC, the p69-containing liquid can optionally be frozen for storage. The frozen material can be thawed and then proceed to IMAC.

Thus the invention can start with *B. pertussis* cells or with material derived from *B. pertussis* cells. The p69 antigen may be purified from a mixture, where the mixture is selected from the group consisting of: (i) *B. pertussis* cellular solids; (ii) a *B. pertussis* lysate; (iii) *B. pertussis* cellular solids that have been treated to release p69 pertactin; (iv) soluble material obtained after treating *B. pertussis* cellular solids to release p69 pertactin; or (v) a mixture comprising a plurality of *B. pertussis* proteins, including p69.

Ideally, the mixture does not contain any bacterial substances from a non-pertussis bacterium e.g. it does not contain any *E. coli* proteins, lipids or saccharides.

Bordetella pertussis Strains

Processes of the invention can be used to purify p69 pertactin from *B. pertussis* cells. The invention can be used with any strain of *B. pertussis* suitable for aP vaccine manufacture. Known strains for this purpose include Tohama strains, Saadet strains, Wellcome 28 (W28) strains, etc. The strain will usually express PT, FHA and pertactin e.g. it may be a phase I strain.

The strain may express wild-type or mutant pertactin. It will typically express a wild-type pertactin, which may be any of alleles prnA1, prnA2, prnA3, prnA4, prnA5 or prnA6 or any other allele (e.g. GI numbers GI:3641851, GI:3641855, GI:3641871, GI:3641847, GI:3641849, GI:4127545). The pertactin ideally does not include a hexa-histidine amino acid sequence tag.

The strain may express wild-type or mutant FHA. It will typically express a wild-type FHA, which may be either of alleles fhaB-1 or fhaB-2 or any other allele (e.g. GI numbers GI:3980255, GI:17154500).

The strain may express wild-type or mutant PT. A wild-type PT may have a S1 subunit of any of alleles ptxS1A, ptxS1B, ptxS1D or ptxS1E as disclosed in reference 9 or any other allele (e.g. GI numbers GI:3152308, GI:3152312, GI:5639718, GI:3152300, GI:22549351, GI:22549355). It is known to modify residues in the S1 subunit of PT to remove its toxic enzymatic activity. A S1 subunit may include more than one such mutation. Known mutations include, but are not limited to, those at residues Arg-9, Asp-11, Arg-13, Trp-26, His-35, Cys-41, Phe-50, Glu-129 and Tyr-130. Typical mutations include Arg-9-Lys, Arg-13-Leu, Trp-26-Ile, Glu-129-Gly. A preferred strain expresses PT having both an Arg-9-Lys mutation and a Glu-129-Gly mutation ('PT-9K/129G'), as disclosed in references 10 and 11. The W28-9K/129G strain [10] can be used.

*B. pertussis* bacteria can be grown in any suitable culture medium, typically an aqueous nutrient medium in aerobic conditions. Media that have been used for culture of vaccine strains include Stainer-Scholte liquid medium and component pertussis broth (CPB). The medium will usually contain glutamate. One or more polyvinyl alcohols (PVA) may be added to the culture medium as this has been reported to increase the yield of PT and FHA [12, 13]. Suitable PVAs may have a molecular weight in the range of 10 kDa to 50 kDa and/or may have a degree of hydrolysis in the range 80 to 90 mol %. Alternatively, the PVAs may have a molecular weight in the range of 1.5 kDa to 16 kDa. One or more cyclodextrins may be added to the medium [14, 15], such as an etherified cyclodextrin e.g. methylcyclodextrin.

The culture medium ideally does not include any animal-derived materials. If animal-derived materials are included (particularly bovine-derived materials) then they should be obtained from sources that are free from transmissible spongiform encephalopathies (TSEs), and in particular free from bovine spongiform encephalopathy (BSE). As an alternative to animal-derived materials then, for example, yeast or soybean extracts can be used [16].

Culture of *B. pertussis* may be prepared in a two-step fermentation involving a first fermentation at a small scale followed by a second fermentation at a large scale, where bacteria from the first fermentation are used to seed the second fermentation.

During bacterial culture, various parameters of the medium may be monitored and/or controlled, such as: temperature, pH, and oxygen concentration.

IMAC

The invention purifies p69 antigen by the use of IMAC. This technique involves the use of a solid support to which a metal ion is immobilised e.g. see reference 17, particularly chapter 10. IMAC is also known as metal-chelate chromatography or metal-ion interaction chromatography.

Typical metal ions used in IMAC are transition metals. Useful ions include Cu(II), Ni(II), Zn(II), Co(II), Fe(II). A preferred metal ion is Ni(II).

The ions may be immobilised in various ways, typically via coordination bonds to an immobilised chelator such as IDA (iminodiacetic acid), NTA (nitrilotriacetic acid), TED (tris (carboxymethyl)ethylene-diamine), TREN (tris(2-aminoethyl)amine), DTPA (diethylenetriamine pentaacetate), carboxymethylated aspartic acid (CM-Asp), TCAN (triazacyclononane), etc. The chelator may be bidentate, tridentate, tetradentate, pentadentate, etc.

Usually, the chelator is covalently attached to a solid support (insoluble matrix), often via a spacer such as epichlorohydrin or bisoxirane. Various such supports are known in the art including, but not limited to, chelating Sepharose, chelating superose, Hi-Trap chelating, chelating Sepharose 6B, chelex, NTA-resin, Novarose Act, TALON superflow, TSK-GEL, Ni-NTA silica, etc.

Examples of suitable IMAC columns include, but are not limited to: POROS™ MC columns, which are based on cross-linked poly(styrene-divinylbenzene) flow-through particles with a bimodal pore size distribution, surface-coated with a cross-linked polyhydroxylated polymer functionalized with IDA; PROPAC™ IMAC columns from DIONEX™, which are high-resolution HPLC columns based on 10 μm nonporous polymeric beads coated with a hydrophilic layer to which poly(IDA) are grafted; SEPHADEX™ columns with IDA groups; SEPHAROSE™ columns based on highly cross-linked agarose with ether-linked IDA groups; etc. Precise flow characteristics, and the concentration of p69 in the eluate, will vary according to the chosen column but preliminary experiments can readily identify suitable operating conditions which can then be subjected to optimisation.

The IMAC is performed such that p69 antigen is retained on the chromatography support. The p69 antigen may then be eluted from the support to provide purified antigen. Any suitable elution scheme can be used including a pH change and/or addition of competing agents (e.g. electron donors, such as imidazole, histidine, etc.). Elution by using imidazole is typical, such as via an imidazole gradient (e.g. a 1 to 25 mM gradient, such as a step gradient).

Further Antigen Treatment

After elution from the IMAC column, p69 antigen may be subjected to further purifications e.g. filtration, concentration, etc.

For instance, the antigen may be subjected to one or more steps of hydrophobic interaction chromatography (HIC). HIC columns use a variety of support matrix materials (e.g. methacrylate, cross-linked agarose) and a variety of functional groups (e.g. ether, butyl, hexyl, phenyl, octyl, methyl). Suitable HIC materials include, but are not limited to: TOYOPEARL™ Butyl-650M; SEPHAROSE™ columns with phenyl, butyl or octyl groups; SUPELCOSIL LC-HINT™; TSKgel Butyl-NPR™; TSKgel Ether-5PW™; TSKgel Phenyl-5PW™, etc. Preferred HIC columns retain p69. A butyl HIC column is preferred.

The antigen may be subjected to one or more steps of ion exchange chromatography, and in particular anion exchange chromatography (AEC). The ion exchange group may conveniently by a quaternary amine group such as —O—CH$_2$CHOHCH$_2$OCH$_2$CHOHCH$_2$N$^+$(CH$_3$)$_3$ as seen in the Q SEPHAROSE™ product with a highly cross-linked agarose support. Preferred AEC columns do not retain the p69 but instead retain contaminants.

The antigen may be subjected to one or more steps of ultrafiltration/diafiltration. Various membranes may be used, such as those based on regenerated cellulose. A membrane with a cutoff below 50 kDa is ideal, such as 40 kDa, 30 kDa, 20 kDa, 10 kDa or less.

Before being included in a vaccine preparation it is usual to subject p69 antigen to chemical treatment e.g. using glutaraldehyde and/or formaldehyde. Formaldehyde is preferred. Treatment by such aldehydes may occur in the presence of lysine. This treatment can stabilise the p69 antigen, and may also ensure consistency with other aP antigens which are treated in such a manner e.g. PT may be treated in this way to inactivate its toxic activity. The reagents may be removed thereafter e.g. by diafiltration/ultrafiltration, which can also concentrate the antigen.

After IMAC, therefore, a p69-containing preparation may be subjected to HIC, then AEC, then ultrafiltration/diafiltration, then inactivation, and then further ultrafiltration/diafiltration.

Preparation of aP Mixture

Processes of the invention provide purified p69 antigen, optionally in inactivated form. Bulk p69 antigen can be quantified and then mixed in a desired ratio with PT and/or FHA to give aP mixtures. The three antigens can be mixed in any order e.g. start with PT, add FHA, add p69. Thus the invention provides a method for preparing an acellular pertussis antigen composition, comprising a step of combining (i) a p69 antigen purified by a process of the invention with (ii) a pertussis toxin and/or a filamentous hemagglutinin.

These three antigens can be combined in any suitable ratio. The mass ratio of PT:FHA:p69 may, for example, be 1:1:1, 2:1:1, 3:4:4, 25:25:8 (as in the INFANRIX™ products), 16:16:5 (as in the BOOSTRIX™ products), 10:5:3 (as in the DAPTACEL™ product), 5:10:6 (as in the ADACEL™ product), etc.

A useful aP mixture has 10 μg/ml PT (preferably 9K/129G mutant), 5 μg/ml FHA and 5 μg/ml p69. Another useful aP mixture has 5 μg/ml PT (preferably 9K/129G mutant), 2.5 μg/ml FHA and 2.5 μg/ml p69.

If an aP mixture is to include non-active pharmaceutical ingredients (e.g. adjuvant, preservative, buffer, tonicity agents, etc.; see below) these may be incorporated before, during or after forming the aP mixture. For instance, in one embodiment a saline solution is formed, to which preservative is added. Adjuvant is then added, and the aP antigens are then added. Where the adjuvant includes an adsorptive aluminium salt then it is typical to add antigens to the adjuvant rather than to add adjuvant to the antigens.

A useful adjuvanted aP mixture has 10 μg/ml PT (preferably 9K/129G mutant), 5 μg/ml FHA, 5 μg/ml p69, 2 mg/ml aluminium hydroxide, 9 mg/ml sodium chloride and 0.1 mg/ml thimerosal. Another useful adjuvanted aP mixture has 5 μg/ml PT (preferably 9K/129G mutant), 2.5 μg/ml FHA, 2.5 μg/ml p69, 2 mg/ml aluminium hydroxide, 9 mg/ml sodium chloride and 0.1 mg/ml thimerosal.

Combinations with Non-Pertussis Antigens

Vaccines including only aP antigens are uncommon, and they usually include antigens for protecting against more than just whooping cough. Inclusion of antigens for protecting against at least diphtheria and tetanus is normal (DTaP mixtures), but further antigens may also be added e.g. for protecting against poliomyelitis, hepatitis B, *H. influenzae* type B meningitis, meningococcal meningitis, pneumococcal meningitis, etc.

Antigens for protecting against such further diseases can be combined with the aP antigens in any suitable order. For example, it is possible in some embodiments to make a mixed aP bulk including two or more aP antigens (e.g. containing all of PT, FHA and p69, as described above) and either add this mixed aP bulk to a non-pertussis antigen or add a non-pertussis antigen to this mixed aP bulk. In other embodiments the aP antigens may be used individually, rather than as a mixed aP bulk.

The invention provides a method for preparing a multi-antigen composition, comprising a step of combining (i) a p69 antigen purified by a process of the invention with (ii) a non-pertussis antigen. The method may also include a step of combining (iii) a non-antigen component.

The invention also provides a multi-antigen composition, comprising (i) a p69 antigen purified by a process of the invention, and (ii) a non-pertussis antigen. The composition is an immunogenic composition such as a vaccine composition. The composition may also include a non-antigen component.

The invention also provides a method for preparing a multi-antigen composition, comprising a step of combining (i) an acellular pertussis antigen composition prepared by a process of the invention with (ii) a non-pertussis antigen. The method may also include a step of combining (iii) a non-antigen component.

The invention also provides a multi-antigen composition, comprising (i) an acellular pertussis antigen composition prepared by a process of the invention, and (ii) at least one non-pertussis antigen. The composition is an immunogenic composition such as a vaccine composition. The composition may also include a non-antigen component.

A p69 antigen purified by processes of the invention, or an acellular pertussis antigen composition, may be combined with a diphtheria toxoid. In some multi-antigen embodiments, however, diphtheria toxoid is absent. Diphtheria is caused by *Corynebacterium diphtheriae*. This organism expresses a prophage-encoded ADP-ribosylating exotoxin ("diphtheria toxin"), which can be treated (e.g. using formaldehyde) to give a toxoid that is no longer toxic but that remains antigenic and is able to stimulate the production of specific anti-toxin antibodies after injection. Diphtheria toxoids are disclosed in more detail in chapter 13 of reference 18. Quantities of diphtheria toxoid can be expressed in international units (IU). For example, the NIBSC [19] supplies the "Diphtheria Toxoid Adsorbed Third International Standard 1999" [20, 21], which contains 160 IU per ampoule. As an alternative to the IU system, the Lf unit ("flocculating units", the "limes flocculating dose", or the "limit of flocculation") is defined as the amount of toxoid which, when mixed with one International Unit of antitoxin, produces an optimally flocculating mixture [22]. For example, the NIBSC supplies "Diphtheria Toxoid, Plain" [23], which contains 300 Lf per ampoule and "The 1st International Reference Reagent For Diphtheria Toxoid For Flocculation Test" [24] which contains 900 Lf per ampoule. The conversion between IU and Lf systems depends on the particular toxoid preparation.

A p69 antigen purified by processes of the invention, or an acellular pertussis antigen composition, may be combined with a tetanus toxoid. In some multi-antigen embodiments, however, tetanus toxoid is absent. Tetanus is caused by *Clostridium tetani*. This organism expresses an endopeptidase ("tetanus toxin"), which can be treated to give a toxoid that is no longer toxic but that remains antigenic and is able to stimulate the production of specific anti-toxin antibodies after injection. Tetanus toxoids are disclosed in more detail in chapter 27 of reference 18. Quantities of tetanus toxoid can be expressed in international units (IU). For example, the NIBSC [19] supplies the "Tetanus Toxoid Adsorbed Third International Standard 2000" [25, 26], which contains 469 IU per ampoule. As an alternative to the IU system, the Lf unit is defined as the amount of toxoid which, when mixed with one International Unit of antitoxin, produces an optimally flocculating mixture [22]. For example, the NIBSC supplies "The 1st International Reference Reagent for Tetanus Toxoid For Flocculation Test" [27] which contains 1000 Lf per ampoule. The conversion between IU and Lf systems depends on the particular toxoid preparation.

A p69 antigen purified by processes of the invention, or an acellular pertussis antigen composition, may be combined with a hepatitis B virus surface antigen (HBsAg). In some multi-antigen embodiments, however, HBsAg is absent. Hepatitis B virus (HBV) is one of the known agents that causes viral hepatitis. The HBV virion consists of an inner core surrounded by an outer protein coat or capsid. The viral core contains the viral DNA genome. The major component of the capsid is a protein known as HBV surface antigen or, more commonly, "HBsAg". All existing hepatitis B vaccines contain HBsAg, and when this antigen is administered to a vaccinee it stimulates the production of anti-HBsAg antibodies which protect against HBV infection. For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention may be prepared in either way, but it is preferred to use FlBsAg which has been recombinantly expressed e.g. in a yeast, such as a *Saccharomyces* e.g. in *S. cerevisiae*. Unlike native HBsAg (i.e. as in the plasma-purified product), yeast-expressed HBsAg is generally non-glycosylated, and this is the most preferred form of HBsAg for use with the invention.

Yeast-expressed HBsAg is advantageously in the form of substantially-spherical particles (average diameter of about 20 nm), including a lipid matrix comprising phospholipids. Unlike plasma-derived HBsAg particles, yeast-expressed particles may include phosphatidylinositol. Moreover, the lipid matrix may include a non-ionic surfactant, such as polysorbate 20, which may be incorporated into the matrix during purification of the antigen from a yeast expression host. Using polysorbate 20 during disruption of recombinant yeast cells at the start of HBsAg purification is one way in which it can be introduced into the HBsAg particles. Quantities of HBsAg are typically expressed in µg.

All known HBV subtypes contain the common determinant 'a'. Combined with other determinants and subdeterminants, nine subtypes have been identified: ayw1, ayw2, ayw3, ayw4, ayr, adw2, adw4, adrq– and adrq+. Besides these subtypes, other variants have emerged, such as HBV mutants that have been detected in immunised individuals ("escape mutants"). The most preferred HBV subtype for use with the invention is subtype adw2.

A p69 antigen purified by processes of the invention, or an acellular pertussis antigen composition, may be combined with an inactivated poliovirus antigen ('IPV'). In some multi-antigen embodiments, however, IPV is absent. Poliomyelitis can be caused by one of three types of poliovirus. The three types are similar and cause identical symptoms, but they are antigenically very different and infection by one type does not protect against infection by others. As explained in chapter 24 of reference 18, it is therefore preferred to use more than one poliovirus antigen in the process of the invention i.e. 2 or 3 of poliovirus Type 1 (e.g. Mahoney strain), poliovirus Type 2 (e.g. MEF-I strain), and/or poliovirus Type 3 (e.g. Saukett strain). Polioviruses may be grown in cell culture. A preferred culture uses a Vero cell line, which is a continuous cell line derived from monkey kidney. Vero cells can conveniently be cultured microcarriers. Culture of the Vero cells before and during viral infection may involve the use of bovine-derived material, such as calf serum, and of lactalbumin hydrolysate (e.g. obtained by enzymatic degradation of lactalbumin). Such bovine-derived material should be obtained from sources which are free from BSE or other TSEs. After growth, virions may be purified using techniques such as ultrafiltration, diafiltration, and chromatography. Prior to administration to patients, polioviruses must be inactivated, and this can be achieved by treatment with formaldehyde before the viruses are used in a process of the invention. The viruses are preferably grown, purified and inactivated individually, and are then combined to give a bulk mixture for use in a process of the invention. Quantities of poliovirus are typically expressed in the "DU" unit ("D-antigen unit" [28]).

A p69 antigen purified by processes of the invention, or an acellular pertussis antigen composition, may be combined with a conjugated capsular saccharide from *Haemophilus influenzae* type B ('Hib'). In some multi-antigen embodiments, however, Hib saccharide is absent. The capsular saccharide may be conjugated to a carrier protein such as tetanus toxoid, diphtheria toxoid, the CRM197 derivative of diphtheria toxoid, *H. influenzae* protein D, or an outer membrane protein complex from serogroup B meningococcus. The saccharide moiety of the conjugate may comprise full-length polyribosylribitol phosphate (PRP) as prepared from Hib bacteria, and/or fragments of full-length PRP. Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5.

A p69 antigen purified by processes of the invention, or an acellular pertussis antigen composition, may be combined with a conjugated capsular saccharide from *Neisseria meningitidis*. In some multi-antigen embodiments, however, meningococcal saccharide is absent. The combination may be with saccharides from more than one meningococcal serogroup e.g. from 1, 2, 3 or all 4 of serogroups A, C, W135 and/or Y ('MenA', 'MenC', 'MenW135' and/or 'MenY'). Typical carrier proteins are tetanus toxoid, diphtheria toxoid, the CRM 197 derivative of diphtheria toxoid, and *H. influenzae* protein D. The saccharide moiety of the conjugate may comprise full-length saccharide as prepared from meningococci, and/or fragments thereof. Serogroup C saccharides may be prepared from either OAc+ or OAc– strains. For serogroup A saccharides, preferably at least 50% (e.g. at least 60%, 70%, 80%, 90%, 95% or more) of the mannosamine residues are O-acetylated at the C-3 position. Meningococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1.

A p69 antigen purified by processes of the invention, or an acellular pertussis antigen composition, may be combined with a conjugated capsular saccharide from *Streptococcus*

*pneumoniae*. In some multi-antigen embodiments, however, pneumococcal saccharide is absent. The combination may be with saccharides from more than one serotype of *S. pneumoniae*, for example at least serotypes 6B, 14, 19F and 23F. Further serotypes are preferably selected from: 1, 3, 4, 5, 7F, 9V and 18C. For example, mixtures of polysaccharides from 23 different serotype are widely used, as are conjugate vaccines with polysaccharides from between 5 and 11 different serotypes [29]. For example, Prevnar™ [30] contains conjugated antigens from seven serotypes (4, 6B, 9V, 14, 18C, 19F, and 23F). Typical carrier proteins are tetanus toxoid, diphtheria toxoid, the CRM197 derivative of diphtheria toxoid, and *H. influenzae* protein D.

Thus p69 antigen purified by processes of the invention may be included in a combination vaccine selected from, but not limited to, the following: D-aP; D-T-aP; D-aP-HBsAg; D-aP-IPV; D-aP-Hib; D-T-aP-HBsAg; D-T-aP-IPV; D-T-aP-Hib; D-aP-HBsAg-IPV; D-aP-HBsAg-Hib; D-aP-Hib-IPV; D-T-aP-HBsAg-IPV; D-T-aP-HBsAg-Hib; D-T-aP-Hib-IPV; D-aP-HBsAg-IPV-Hib; D-T-aP-HBsAg-IPV-Hib, etc. Meningococcal and/or pneumococcal saccharide conjugates may also be added. Further combinations are also possible e.g. to protect against Japanese encephalitis virs, yellow fever virus, etc.

In some embodiments of the invention, therefore, a vaccine includes an aP mixture in combination with diphtheria toxoid and tetanus toxoid (and, optionally, one or more further antigens such as IPV). In such embodiments, the ratio of diphtheria toxoid to tetanus toxoid, measured in Lf units, can vary. For instance, it may be greater than 1 (e.g. 2.5 or 3), it may be substantially 1, or it may be less than 1 (e.g. 0.4 or 0.5). A D:T ratio above 1 is typical for pediatric use (e.g. as in the INFANRIX™ series and DAPTACEL™ products), whereas a D:T ratio below 1 is typical for adolescent or adult use (e.g. as in the BOOSTRIX™, BOOSTRIX-IPV™ and ADACEL™ products).

Thus a vaccine of the invention may have 20 Lf/ml tetanus toxoid, 50 Lf/ml diphtheria toxoid, 10 µg/ml PT (preferably 9K/129G mutant), 5 µg/ml FHA and 5 µg/ml p69. Another vaccine of the invention may have 10 Lf/ml tetanus toxoid, 25 Lf/ml diphtheria toxoid, 5 µg/ml PT (preferably 9K/129G mutant), 2.5 µg/ml FHA and 2.5 µg/ml p69. Another vaccine of the invention may have 10 Lf/ml tetanus toxoid, 30 Lf/ml diphtheria toxoid, 5 µg/ml PT (preferably 9K/129G mutant), 2.5 µg/ml FHA and 2.5 µg/ml p69. Another vaccine of the invention may have 20 Lf/ml tetanus toxoid, 50 Lf/ml diphtheria toxoid, 5 µg/ml PT (preferably 9K/129G mutant), 2.5 µg/ml FHA and 2.5 µg/ml p69. Another vaccine of the invention may have 10 Lf/ml tetanus toxoid, 5 Lf/ml diphtheria toxoid, 10 µg/ml PT (preferably 9K/129G mutant), 5 µg/ml FHA and 5 µg/ml p69. Another vaccine of the invention may have 10 Lf/ml tetanus toxoid, 4 Lf/ml diphtheria toxoid, 5 µg/ml PT (preferably 9K/129G mutant), 2.5 µg/ml FHA and 2.5 µg/ml p69. Another vaccine of the invention may have between 5-15 Lf/ml tetanus toxoid, between 2-8 Lf/ml diphtheria toxoid, between 1-20 µg/ml PT preferably as the 9K/129G mutant, between 1-20 µg/ml FHA, and 1-20 µg/ml p69.

In a single unit dose, therefore, a vaccine of the invention may have 10 Lf tetanus toxoid, 25 Lf diphtheria toxoid, 5 µg PT (preferably 9K/129G mutant), 2.5 µg FHA and 2.5 µg p69. Another vaccine of the invention may have 5 Lf tetanus toxoid, 12.5 Lf diphtheria toxoid, 2.5 µg PT (preferably 9K/129G mutant), 1.25 µg FHA and 1.25 µg p69. Another vaccine of the invention may have 5 Lf tetanus toxoid, 15 Lf diphtheria toxoid, 2.5 µg PT (preferably 9K/129G mutant), 1.25 µg FHA and 1.25 µg p69. Another vaccine of the invention may have 10 Lf tetanus toxoid, 25 Lf diphtheria toxoid, 2.5 µg PT (preferably 9K/129G mutant), 1.25 µg FHA and 1.25 µg p69. Another vaccine of the invention may have 5 Lf tetanus toxoid, 2.5 Lf diphtheria toxoid, 5 µg PT (preferably 9K/129G mutant), 2.5 µg FHA and 2.5 µg p69. Another vaccine of the invention may have 5 Lf tetanus toxoid, 2 Lf diphtheria toxoid, 2.5 µg PT (preferably 9K/129G mutant), 1.25 µg FHA and 1.25 µg p69. Another vaccine of the invention may have between 2.5-7.5 Lf tetanus toxoid, between 1-4 Lf diphtheria toxoid, between 0.5-10 µg PT preferably as the 9K/129G mutant, between 0.5-10 µg FHA, and 0.5-10 µg p69.

Non-active pharmaceutical ingredients (e.g. adjuvant, preservative, buffer, tonicity agents, etc.; see below) may be incorporated at any stage during mixing of the various components e.g. before, during or after using a p69 antigen of the invention. For instance, in one embodiment for making a D-T-aP vaccine, a saline solution is formed, to which preservative (e.g. thimerosal) is added. Adjuvant is then added. Diphtheria toxoid is then added, then tetanus toxoid, and then aP antigens (e.g. PT, then FHA, then p69). This process can be used to make a vaccine having 20 Lf/ml tetanus toxoid, 50 Lf/ml diphtheria toxoid, 10 µg/ml PT (preferably 9K/129G mutant), 5 µg/ml FHA, 5 µg/ml p69, 2 mg/ml aluminium hydroxide, 9 mg/ml sodium chloride and 0.1 mg/ml preservative.

Pharmaceutical Compositions

Antigens prepared by a process of invention may be combined with at least one non-antigen component e.g. in the formulation of pharmaceutical compositions. For example, the non-antigen component(s) may be pharmaceutical carrier(s) and/or excipient(s). A discussion of such components is available in reference 36.

The invention provides a method for preparing a composition, comprising a step of combining (i) a p69 antigen purified by a process of the invention with (ii) a non-antigen component. The method may also include a step of combining (iii) a non-p69 aP antigen and/or (iv) a non-pertussis antigen.

The invention also provides a composition, comprising (i) a p69 antigen purified by a process of the invention, and (ii) a non-antigen component. The composition is an immunogenic composition such as a vaccine composition. The composition may also include a non-p69 aP antigen and/or a non-pertussis antigen.

In some embodiments the non-antigenic component can comprise a preservative, such as thiomersal or 2-phenoxyethanol. The inclusion of a preservative is preferred if a composition is packaged in a multi-dose container.

In some embodiments the non-antigenic component can comprise an agent to control tonicity. Thus a composition may include a physiological salt, such as a sodium salt. Sodium chloride (NaCl) is preferred, which may be present at between 1 and 20 mg/ml e.g. about 9±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

In some embodiments the non-antigenic component can comprise a buffer. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

In some embodiments the non-antigenic component can comprise a temperature protective agent. This component may be particularly useful in adjuvanted compositions (particularly those containing a mineral adjuvant, such as an aluminium salt). As described in reference 31, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

In some embodiments the non-antigenic component can comprise a vaccine adjuvant. Any suitable adjuvants can be used e.g. an oil-in-water emulsion, a mineral-containing composition, a saponin, a monophosphoryl lipid A, an imidazoquinolone, a substituted urea, an aminoalkyl glucosaminide, a TLR4 ligand, a TLR9 ligand, etc.

One preferred class of adjuvants for inclusion in compositions of the invention is mineral-containing compositions, such as aluminum salts and calcium salts (or mixtures thereof). Calcium salts include calcium phosphate (e.g. the "CAP" particles disclosed in ref. 32). Aluminum salts include hydroxides, phosphates, sulfates, etc., with the salts taking any suitable form (e.g. gel, crystalline, amorphous, etc.). Adsorption of antigens to these salts is typical [33] but is not always necessary. The mineral containing compositions may also be formulated as a particle of metal salt [34].

The adjuvants known as aluminum hydroxide and aluminum phosphate may be used. These names are conventional, but are used for convenience only, as neither is a precise description of the actual chemical compound which is present (e.g. see chapter 9 of reference 35). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4$/Al molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Compositions are typically sterile.

Compositions are preferably non-pyrogenic e.g. containing <1 EU (endotoxin unit, a standard measure) per dose, and preferably <0.1 EU per dose.

Compositions are preferably gluten-free.

Compositions are preferably free of bovine-sourced components.

Human vaccines are typically administered in a dosage volume of about 0.5 ml, although a half dose (i.e. about 0.25 ml) may be administered to children.

A useful composition of the invention has 10 μg/ml PT (preferably 9K/129G mutant), 5 m/ml FHA, 5 μg/ml p69, 2 mg/ml aluminium hydroxide, 9 mg/ml sodium chloride and 0.1 mg/ml thimerosal. It may also include non-pertussis antigens e.g. 20 Lf/ml tetanus toxoid and/or 50 Lf/ml.

Methods of Treatment, and Administration of Immunogenic Compositions

The invention provides a method for raising an immune response in a mammal comprising the step of administering an effective amount of a composition of the invention. The immune response is preferably protective and preferably involves antibodies and/or cell-mediated immunity. The method may raise a booster response.

The invention also provides a p69 antigen purified by a process of the invention for use as a medicament e.g. for use in raising an immune response in a mammal.

The invention also provides the use of a p69 antigen purified by a process of the invention in the manufacture of a medicament for raising an immune response in a mammal.

By raising an immune response in the mammal by these uses and methods, the mammal can be protected against at least whooping cough.

The mammal is preferably a human. Where the vaccine is for prophylactic use, the human is preferably a child (e.g. a toddler or infant) or a teenager or an adult; where the vaccine is for therapeutic use, the human is preferably a teenager or an adult. A vaccine intended for children may also be administered to adults e.g. to assess safety, dosage, immunogenicity, etc. Methods for assessing the efficacy of acellular pertussis vaccines in humans are well known in the art. Vaccine compositions can also be assessed by using animal models or in vitro tests.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration. Intramuscular injection is usual.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines prepared according to the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pneumococcal conjugate vaccine, a conjugated *H. influenzae* type b vaccine, an inactivated poliovirus vaccine, a hepatitis B virus vaccine (including a combined hepatitis A & B virus vaccine), a meningococcal conjugate vaccine (such as a tetravalent A-C-W135-Y vaccine), a respiratory syncytial virus vaccine, a travel vaccine (such as a yellow fever vaccine, a cholera vaccine, a japanese encephalitis vaccine, a rabies vaccine, a typhoid vaccine), etc.

The invention also provides a delivery device pre-filled with an immunogenic composition of the invention.

The invention also provides a kit comprising a first component and a second component wherein the first component and the second component can be combined to provide a composition of the invention as described above. The first and second components may each be in vials, but in some embodiments one component is in a pre-filled syringe. The kit may further include a third component comprising one or more of the following: instructions, syringe or other delivery device, adjuvant, or pharmaceutically acceptable formulating solution. One or more antigen-containing components in such a kit may be lyophilised. For instance, it is known to lyophilise Hib and/or meningococcal saccharide conjugates for extemporaneous reconstitution with other liquid antigen components (e.g. with a D-T-aP-containing mixture, as in INFANRIX-HEXA™) to provide a final vaccine for administration to a patient. Thus, for example, the invention provides kits for preparing multi-antigen compositions mentioned above, wherein a first kit component is a D-aP, D-T-aP, D-aP-1-1BsAg, D-aP-IPV, D-T-aP-HBsAg, D-T-aP-IPV, D-aP-HBsAg-IPV, or D-T-aP-HBsAg-IPV composition and a second kit component includes one or more lyophilised saccharide conjugates e.g. the second kit component is a Hib, Hib-MenC, Hib-MenC-MenY, MenA, MenC, MenW135, MenY, MenC-MenY, MenA-MenC-MenW135-MenY, or Hib-MenA-MenC-MenW135-MenY composition. Each and every individual combination of such first and second kit components is disclosed herein.

Modifications and Derivatives of the Above Process

The invention also provides processes starting at or ending with intermediates in the above processes.

Thus the invention provides a process for purifying p69 antigen from *Bordetella pertussis* bacteria, comprising steps of: (a) treating cellular solids to release p69 pertactin therein, wherein the cellular solids were obtained by separating a culture of *Bordetella pertussis* cells into a supernatant liquid and pertactin-containing cellular solids; (b) contacting the released p69 with a support comprising an immobilised metal ion, to give an eluate and a p69-containing retentate; and (c) eluting p69 from the retentate to provide purified p69.

The invention also provides a process for purifying p69 antigen from *Bordetella pertussis* bacteria, comprising steps of: (a) contacting a p69-containing mixture with a support comprising an immobilised metal ion, to give an eluate and a p69-containing retentate, wherein the p69-containing mixture was obtained by separating a culture of *Bordetella pertussis* cells into a supernatant liquid and pertactin-containing cellular solids and releasing p69 therein; and (b) eluting p69 from the retentate to provide purified p69.

The invention also provides a process for purifying p69 antigen from *Bordetella pertussis* bacteria, comprising steps of: (a) contacting a p69-containing mixture with a support comprising an immobilised metal ion, to give an eluate and a p69-containing retentate, wherein the p69-containing mixture was obtained by releasing p69 from cellular solids obtained by separating a culture of *Bordetella pertussis* cells into a supernatant liquid and pertactin-containing cellular solids; and (b) eluting p69 from the retentate to provide purified p69.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional but means, for example, x±10%.

Different steps in a method of the invention can optionally be performed at different times by different people in different places (e.g. in different countries).

The practice of the present invention will employ, unless otherwise indicated, conventional methods of chemistry, biochemistry, molecular biology, immunology and pharmacology, within the skill of the art. Such techniques are explained fully in the literature. See, e.g., references 36-43, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

MODES FOR CARRYING OUT THE INVENTION

Figure 1:
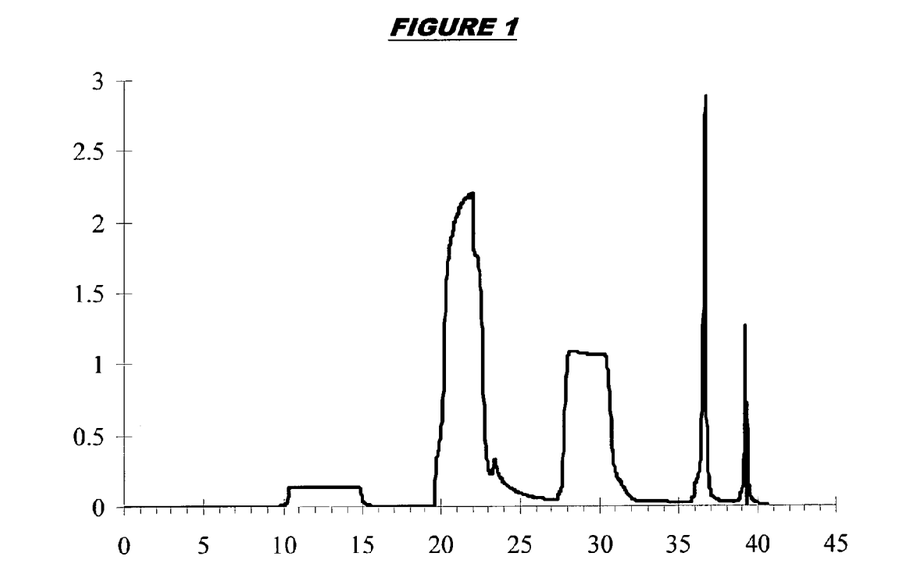
FIG. 1 is a chromatogram of an IMAC experiment, showing the UV response against column volumes. From CV 0-5 is washing, then from 5-10 and 10-15 are charging. 15-19 is equilibration, then 19-23 is flow-through after product addition. 23-26, 26-30 and 30-33 are washings steps, then 33-37 is 69 KDa elution. 37-40 is stripping.
Figure 2:
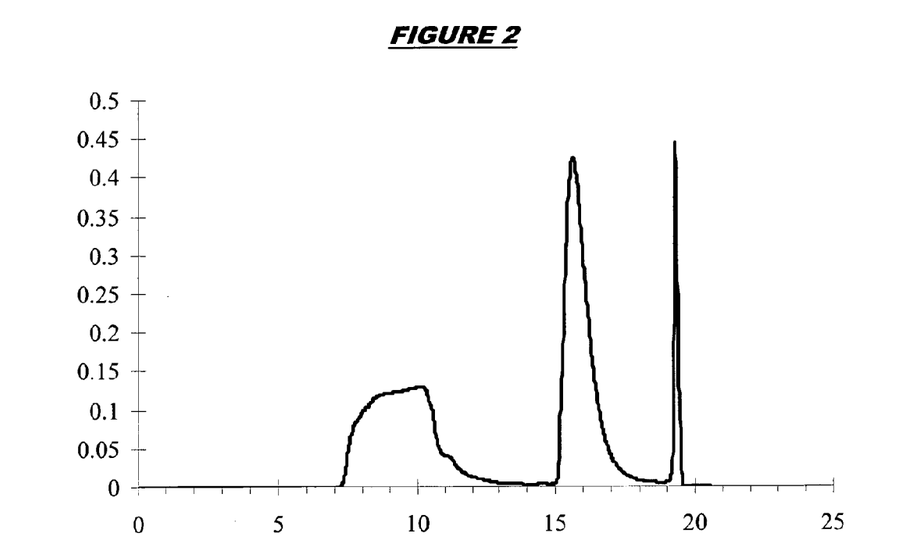
FIG. 2 is a chromatogram of a Butyl column experiment. Sample is loaded at 7 CV and eluted between 14-18 CV.
Figure 3:
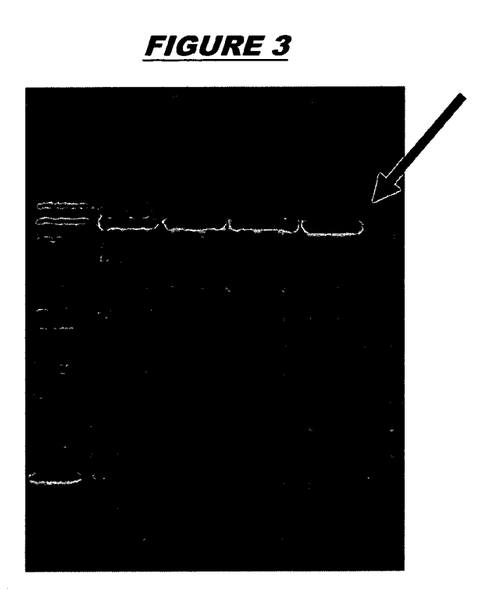
FIG. 3 is a SDS-PAGE gel from the FIG. 2 experiment. The arrow shows purified 69 kDa pertactin after diafiltration/ultrafiltration.

A concentrated *B. pertussis* cell extract is prepared containing about 20 g 69 kDa pertactin. The concentrate is adjusted to include 20 mM $NaPO_4$/150 mM NaCl/1 mM Imidazole/pH 7.5. The conductivity at this point is confirmed to be 15.8±1.0 mS/cm at 20° C.

The material is filtered in two stages: first with a 0.8/0.2 μm Sartorious Sartobran P™ filter, and then with a 0.2 μm Millipore Durapore™ filter. The filtrate may be held at room temperature after filtration for up to 24 hours or stored at 2-8° C. before continuing processing.

The 69 kDa concentration in the filtrate can be tested at this point.

A Pharmacia™ Chelating Sepharose Fast Flow Media™ column (14 L, 30 cm dia.×20 cm high) is rinsed free of any storage solution using ≥1.5 column volumes (CV) of WFI. It is then washed with ≥5 CV of Nickel Charge Buffer (20 mM $NaPO_4$/50 mM $NiCl_2$/pH 4.0±0.2/10.5±1.5 mS/cm @ 20° C.). It is then washed with ≥5 CV of Imidazole Charge Buffer (20 mM $NaPO_4$/200 mM Imidazole/pH 7.5±0.1, 7.1±0.3 mS/cm). It is then equilibrated with ≥5 CV of Equilibration/Wash 1/Wash 3 Buffer (20 mM $NaPO_4$/150 mM NaCl/1 mM Imidazole/pH 7.5±0.1/15.8±0.5 mS/cm). Equilibration is confirmed by ensuring that the pH and conductivity of the effluent match those of the Equilibration Buffer. All of these column steps can be run at ≤150 cm/hr.

The filtrate is loaded onto the column. Capacity is 1.6 g 69 k per liter of media. There is a first wash with the Equilibration/Wash 1/Wash 3 Buffer (≥5 CV) until the effluent is clean. There is a second wash with ≥3 CV of Wash 2 Buffer (20 mM $NaPO_4$/150 mM NaCl/1 mM Imidazole/1% Triton/pH 7.5±0.1/15.7±0.6 mS/cm). Then there is a third wash with the Equilibration/Wash 1/Wash 3 Buffer (≥3.5 CV) until the effluent is clean. Elution occurs by addition of Elution Buffer (20 mM $NaPO_4$/150 mM NaCl/25 mM Imidazole/pH 7.5±0.1/15.9±0.6 mS/cm). At least 5 CV are used for elution and the complete elution peak is collected. Finally, the column is stripped using strip buffer (0.25 M EDTA/2.0 M NaCl/pH 8.0±0.2). Except for the stripping step, these product purification steps are performed at 150 cm/hr.

The eluted material is adjusted to 50 mM Tris/250 mM $NH_4SO_4$/pH 8.8. If necessary pH is maintained at 8.8 using concentrated HCl or 50% NaOH. Conductivity is ≤50 mS/cm. Material is filtered with 0.2 μm Millipore Durapore™ into a container for loading onto a Butyl 650 M column. The product may be held at room temperature after filtration for up to 24 hours or stored at 2-8° C. before continuing processing.

FIG. 1 shows a chromatogram of this IMAC process. The 69 kDa pertactin protein is highly enriched by this IMAC step and is the strongest visible band when the eluate is visualised by SDS-PAGE. Further processing of the eluate achieves even higher purity of the protein.

For instance, the eluate is loaded onto a Tosohaas™ Butyl 650 M Media column equilibrated with 50 mM Tris/0.25 M $NH_4SO_4$/pH 8.8±0.1. Elution occurs by reducing the $NH_4SO_4$ concentration to 0.1 M. FIG. 2 shows a chromatogram and FIG. 3 shows the purified material.

Further purification steps can be performed. For instance, the Butyl eluate is loaded onto Pharmacia Q Sepharose Fast Flow Media™ and the flow-through is retained. Ultrafiltration/diafiltration is then used with a Millipore Pellicon II™, 10 KD MWCO Regenerated Cellulose Membrane.

FIG. 3 shows the purified material.

The purified material is inactivated using lysine-HCl (5 g/l) and formaldehyde (40% W/V) at 33-37° C. for 48±1 hours with slow stirring. The inactivated material is again subjected to diafiltration/ultrafiltration to remove lysine and formaldehyde. The product appears as a single peak by size exclusion HPLC.

Both nickel and endotoxin were undetectable in the final product and no bioburden was identified at any point. Overall recovery is about 60% and the process takes about 8 days. In contrast, prior art methods can give only 25% recovery after 16 days.

This process was tested at 43% of full scale on full scale equipment. The test run processed 8.5 g 69 k and yielded 5.0 g 69 k for an overall recovery of 59%. The process performed as expected and the purified product met all bulk release specifications tested.

The above description of preferred embodiments of the invention has been presented by way of illustration and example for purposes of clarity and understanding. It is not exhaustive and the invention is not limited to the precise forms disclosed. It will be readily apparent to those of ordinary skill in the art in light of the teachings of this invention that many changes and modifications may be made thereto without departing from the spirit of the invention.

REFERENCES

[1] U.S. Pat. No. 4,997,915.
[2] Tan et al. (1991) *Mol Immunol* 28:251-5.
[3] U.S. Pat. No. 5,444,159.
[4] U.S. Pat. No. 5,877,298
[5] U.S. Pat. No. 6,399,076.
[6] WO95/29934.
[7] Montaraz et al. (1985) *Infect Immun* 47:744-51.
[8] Charles et al. (1994) *Microbiology* 140:3301-8.

[9] Mooi et al, 2000, Eur J Clin Microbiol Infect Dis, 19: 174-18
[10] EP-0462534.
[11] Podda et al. (1990) *J Exp Med* 172(3):861-8.
[12] U.S. Pat. No. 4,551,429
[13] WO97/17427.
[14] U.S. Pat. No. 4,500,639.
[15] U.S. Pat. No. 4,687,738.
[16] US-2005/0089968.
[17] *Handbook of Affinity Chromatography* (2006, 2nd edition) ed. Hage. ISBN 978-0-8247-4057-3.
[19] National Institute for Biological Standards and Control; Potters Bar, UK. nibsc.ac.uk
[19] National Institute for Biological Standards and Control; Potters Bar, UK. www.nibsc.ac.uk
[20] Sesardic et al. (2001) *Biologicals* 29:107-22.
[21] NIBSC code: 98/560.
[22] Module 1 of WHO's The immunological basis for immunization series (Galazka).
[23] NIBSC code: 69/017.
[24] NIBSC code: DIFT.
[25] Sesardic et al. (2002) *Biologicals* 30:49-68.
[26] NIBSC code: 98/552.
[27] NIBSC code: TEFT.
[28] Module 6 of WHO'S The immunological basis for immunization series (Robertson).
[29] Zielen et al. (2000) *Infect. Immun.* 68:1435-1440.
[30] Darkes & Plosker (2002) *Paediatr Drugs* 4:609-630.
[31] WO2006/110603.
[32] U.S. Pat. No. 6,355,271.
[33] Poolman & Hallander (2007) *Expert Rev Vaccines* 6:47-56.
[34] WO00/23105.
[35] *Vaccine Design* . . . (1995) eds. Powell & Newman. ISBN: 030644867X. Plenum.
[36] Gennaro (2000) *Remington: The Science and Practice of Pharmacy.* 20th edition, ISBN: 0683306472.
[37] *Methods In Enzymology* (S. Colowick and N. Kaplan, eds., Academic Press, Inc.)
[38] *Handbook of Experimental Immunology*, Vols. I-IV (D. M. Weir and C. C. Blackwell, eds, 1986, Blackwell Scientific Publications)
[39] Sambrook et al. (2001) *Molecular Cloning: A Laboratory Manual,* 3rd edition (Cold Spring Harbor Laboratory Press).
[40] *Handbook of Surface and Colloidal Chemistry* (Birdi, K. S. ed., CRC Press, 1997)
[41] Ausubel et al. (eds) (2002) *Short protocols in molecular biology,* 5th edition (Current Protocols).
[42] *Molecular Biology Techniques: An Intensive Laboratory Course,* (Ream et al., eds., 1998, Academic Press)
[43] *PCR (Introduction to Biotechniques Series),* 2nd ed. (Newton & Graham eds., 1997, Springer Verlag)

The invention claimed is:

1. A process for purifying *Bordetella pertussis* p69 antigen from a *Bordetella pertussis* culture, comprising steps of: (a) separating p69 antigen containing cellular solids from supernatant liquid in the *Bordetella pertussis* culture, (b) treating the p69 antigen containing cellular solids to obtain a p69 antigen containing liquid; (c) contacting the p69 antigen containing liquid with a support comprising an immobilised metal ion, to give an eluate and a p69-containing retentate; (d) eluting p69 from the retentate; and (e) further purifying the eluate obtained by step (d) by hydrophobic interaction chromatography and anion exchange chromatography to provide purified p69, wherein the p69 does not comprise a hexahistidine amino acid sequence tag.

2. The process of claim 1, wherein heat treatment was used to release p69 from the *B. pertussis* cellular solids.

3. The process of claim 1, wherein the *B. pertussis* is a phase I strain.

4. The process of claim 1, wherein the *B. pertussis* expresses pertactin with allele prnA1, prnA2, prnA3, prnA4, prnA5 or prnA6.

5. The process of claim 1, wherein the *B. pertussis* expresses a wild-type pertussis toxin.

6. The process of claim 1, wherein the *B. pertussis* expresses a pertussis toxin having an Arg-9-Lys mutation and a Glu-129-Gly mutation ('PT 9K/129G').

7. The process of claim 1, wherein the p69 antigen containing liquid contains a plurality of *B. pertussis* proteins, including p69.

8. The process of claim 1, wherein the p69 antigen containing liquid does not contain any *E. coli* proteins, lipids or saccharides.

9. The process of claim 1, wherein the metal ion is $Ni^{2+}$.

10. The process of claim 1, wherein p69 is eluted from the retentate using imidazole.

11. The process of claim 1, wherein p69 is further purified by ultrafiltration/diafiltration.

12. The process of claim 1, wherein p69 is inactivated using formaldehyde and/or glutaraldehyde.

* * * * *